United States Patent
Koji et al.

(10) Patent No.: US 12,201,715 B2
(45) Date of Patent: Jan. 21, 2025

(54) PERSONAL CARE COMPOSITION CONTAINING SPHERICAL SILICONE ELASTOMER FINE PARTICLES

(71) Applicant: Momentive Performance Materials Inc., Waterford, NY (US)

(72) Inventors: Suenaga Koji, Gunma (JP); Benjamin Falk, Tarrytown, NY (US); Amar Pawar, Tarrytown, NY (US); Mana Tamami, Tarrytown, NY (US); Linda Wei, Tarrytown, NY (US); Qinghua Li, Kanagawa (JP)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 306 days.

(21) Appl. No.: 17/820,548

(22) Filed: Aug. 17, 2022

(65) Prior Publication Data
US 2024/0058255 A1    Feb. 22, 2024

(51) Int. Cl.
| | |
|---|---|
| *A61K 8/891* | (2006.01) |
| *A61K 8/02* | (2006.01) |
| *A61K 8/27* | (2006.01) |
| *A61K 8/35* | (2006.01) |
| *A61K 8/368* | (2006.01) |
| *A61K 8/40* | (2006.01) |
| *A61Q 1/06* | (2006.01) |
| *A61Q 17/04* | (2006.01) |
| *A61Q 19/00* | (2006.01) |

(52) U.S. Cl.
CPC .............. *A61K 8/891* (2013.01); *A61K 8/025* (2013.01); *A61K 8/27* (2013.01); *A61K 8/35* (2013.01); *A61K 8/368* (2013.01); *A61K 8/40* (2013.01); *A61Q 1/06* (2013.01); *A61Q 17/04* (2013.01); *A61Q 19/00* (2013.01); *A61K 2800/30* (2013.01); *A61K 2800/33* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 4,987,169 | A | 1/1991 | Kuwata et al. |
| 5,654,362 | A | 8/1997 | Schulz et al. |
| 5,760,116 | A | 6/1998 | Kilgour et al. |
| 5,811,487 | A | 9/1998 | Schulz et al. |
| 6,423,322 | B1 | 7/2002 | Fry et al. |
| 2006/0013791 | A1 | 1/2006 | Shimizu et al. |
| 2010/0112023 | A1 | 5/2010 | Inokuchi et al. |
| 2012/0251598 | A1 | 10/2012 | Ikeda et al. |
| 2014/0161758 | A1 | 6/2014 | Tamura et al. |

FOREIGN PATENT DOCUMENTS

JP        4860214 B2    1/2012

OTHER PUBLICATIONS

International Search Report and Written Opinion for Int'l Appl. No. PCT/US2023/029892 mailed Oct. 19, 2023, 9 pages, United States.

*Primary Examiner* — Nannette Holloman
(74) *Attorney, Agent, or Firm* — Sterne, Kessler, Goldstein & Fox P.L.L.C.

(57) ABSTRACT

The present disclosures are directed to personal care compositions comprising crosslinked silicone elastomer; personal care compositions comprising a crosslinked silicone elastomer powder that is free of surfactant; and personal care compositions that are free of a polyether compound. The present disclosures are further directed to personal care compositions comprising one or more of oils, an aqueous phase, sunscreens, film formers, waxes, emulsifiers, particulates, pigments, dyes, and preservatives.

21 Claims, 2 Drawing Sheets

PERSONAL CARE COMPOSITION CONTAINING SPHERICAL SILICONE ELASTOMER FINE PARTICLES

FIELD OF THE DISCLOSURE

The present disclosure relates to personal care compositions comprising a crosslinked silicone elastomer. The present disclosure also relates to personal care compositions comprising a crosslinked silicone elastomer powder that is free of surfactant. The present disclosure further relates to personal care compositions that are free of a polyether compound.

BACKGROUND

Crosslinked silicone elastomers provide luxurious sensory benefits to personal care formulations. These benefits include but are not limited to providing cushioning feel, matte appearance and powdery soft afterfeel. The crosslinked silicone elastomers are often prepared by crosslinking siloxane monomers in the presence of solvents and shearing the mixture by using high shear mixer to form a smooth gel. See for example, U.S. Pat. Nos. 4,987,169; 5,654,362; 5,760,116; 6,423,322; and 5,811,487. These crosslinked elastomers often contain a catalyst such as a platinum or a tin because the reaction is carried out in the presence of such a catalyst. The morphology or shape of the sheared particles is non-uniform and hardly controlled. JP 4860214B describes a method to prepare crosslinked silicone elastomer with uniform spherical morphology and without using platinum or tin catalyst. These silicone elastomers mentioned in JP4860214B, however, are accompanied with surfactants which are used during synthesis. In one aspect, these surfactants can be polyether-based surfactants which are carried into personal care formulations along with the elastomer and can stabilize the personal care formulations. However, polyether compounds and surfactants can often irritate the skin. Therefore, there is a need for personal care formulations containing crosslinked silicone elastomers which are prepared without using platinum or tin catalyst and are free of polyether compounds.

BRIEF SUMMARY OF THE DISCLOSURE

The disclosure provides a personal care composition comprising a crosslinked silicone elastomer prepared by
(1) preparing crosslinkable siloxane by reacting
 (a) α, ω-dihydroxypoly(diorganosiloxane) having a viscosity (25° C.) of about 5 to about 3000 mPa·s; and
 (b) organotrialkoxysilane with a general formula $R^1Si(OR^2)_3$;
 wherein:
 $R^1$ is a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
 $R^2$ is methyl, ethyl, or 2-methoxyethyl;
(2) emulsifying the crosslinkable siloxane in the presence of a surfactant;
(3) crosslinking the emulsified siloxane;
wherein the personal care composition is free of a polyether compound.

The disclosure also provides a personal care composition comprising a crosslinked silicone elastomer prepared by
(1) preparing crosslinkable siloxane by reacting
 (a) α, ω-dihydroxypoly(diorganosiloxane) having a viscosity (25° C.) of about 5 to about 3000 mPa·s; and
 (b) organotrialkoxysilane with a general formula $R^1Si(OR^2)_3$;
 wherein:
 $R^1$ is a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
 $R^2$ is methyl, ethyl, or 2-methoxyethyl;
 wherein the alkoxyl group of component (b) is about 1.5 to about 5 per silanol groups of component (a);
(2) emulsifying the crosslinkable siloxane in the presence of a surfactant;
(3) crosslinking the emulsified siloxane;
wherein the personal care composition is free of a polyether compound.

The disclosure further provides a personal care composition comprising a crosslinked silicone elastomer powder that is spherical and prepared by
(1) preparing crosslinkable siloxane by reacting
 (a) α, ω-dihydroxypoly(diorganosiloxane) having a viscosity (25° C.) of about 5 to about 3000 mPa·s; and
 (b) organotrialkoxysilane with a general formula $R^1Si(OR^2)_3$;
 wherein:
 $R^1$ is a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
 $R^2$ is methyl, ethyl, or 2-methoxyethyl;
(2) emulsifying the crosslinkable siloxane in the presence of a surfactant;
(3) crosslinking the emulsified siloxane to form crosslinked silicone elastomer emulsion; and
(4) drying the crosslinked silicone elastomer emulsion to isolate solid crosslinked silicone elastomer powder;
wherein the personal care composition is free of a polyether compound.

The disclosure further provides a crosslinked silicone elastomer powder that is free of surfactant.

BRIEF DESCRIPTION OF THE FIGURES

The accompanying figures, which are incorporated herein, form part of the specification and illustrate embodiments of the present disclosure. Together with the description, the figures further serve to explain the principles of and to enable a person skilled in the relevant art(s) to make and use the disclosed embodiments. The figures are intended to be illustrative, not limiting.

DETAILED DESCRIPTION

As used above, and throughout the description, the following terms, unless otherwise indicated, shall be understood to have the following meanings.

Unless stated otherwise, the terms "a" and "an" and "the" and similar references used in the context of describing a particular aspect of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein.

Furthermore, "and/or", where used herein, is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The term "about" encompasses the range of experimental error that occurs in any measurement.

The term, "hydrocarbon" as used herein refers to any chemical structure containing hydrogen atoms and carbon atoms.

The term "alkyl" means any monovalent, saturated straight chain or branched chain hydrocarbon group; and the term "alkenyl" means any monovalent straight chain or branched chain hydrocarbon group containing one or more carbon-carbon double bonds where the site of attachment of the group can be either at a carbon-carbon double bond or elsewhere therein.

Representative examples of alkyls include, but are not limited to, methyl, ethyl, propyl and isobutyl. Examples of alkenyls include, but are not limited to, vinyl, propenyl, allyl, methallyl, ethylidenyl norbornane, ethylidene norbornyl, ethylidenyl norbornene and ethylidene norbornenyl.

The term "aryl" includes any aromatic hydrocarbon from which one hydrogen atom has been removed. Specific, non-limiting examples of aryl groups include phenyl and naphthalenyl.

The term "halo" or "halogen" as used by itself or as part of another group refers to —Cl, —F, —Br, or —I.

The term "a polyether compound" includes silicone/organic molecule having ether groups, mainly polyethylene glycol (PEG) and polypropylene glycol (PPG) ether groups. Examples of polyether compounds include, but are not limited to, polyethylene oxide, polypropylene oxide, polybutylene oxide, polyoxyethylene/polyoxypropylene glycol, polyoxyethylene alkyl ethers, polyoxyethylene alkenyl ethers, polyoxyethylene alkylphenyl ethers, and polyoxyethylene/polyoxypropylene alkyl ethers.

The term "surfactant" includes an anionic surfactant, a cationic surfactant, a nonionic surfactant, and a zwitterionic surfactants.

Anionic surfactants include, but are not limited to, hexyl benzene sulfonic acid, octyl benzene sulfonic acid, decyl benzene sulfonic acid, dodecyl benzene sulfonic acid, cetyl benzene sulfonic acid, myristyl benzene sulfonic acid, lauryl sulfate, polyoxyethylene lauryl sulfate, dodecyl sulfonic acid, tetradecene sulphonic acid, hexadecyl sulphonic acid, hydroxydodecane sulfonic acid, hydroxytetradecane sulfonic acid, hydroxyhexadecane sulfonic acid, and their salts thereof.

Cationic surfactants include, but are not limited to, octyltrimethylammonium hydroxide, lauryltrimethylammonium hydroxide, stearyltrimethylammonium hydroxide, dioctyldimethylammonium hydroxide, distearyldimethylammonium hydroxide, lauryltrimethylammonium chloride, stearyltrimethylammonium chloride, cetyltrimethylammonium chloride, dicocoyldimethylammonium chloride, distearyldimethylammonium chloride, benzalkonium chloride, and stearyldimethylbenzylammonium chloride.

Nonionic surfactants include, but are not limited to, polyoxyethylene lauryl ether, polyoxyethylene fatty acid ester, polyoxyethylene sorbitan fatty acid ester, sorbitan fatty acid ester, glycerin fatty acid ester, polyoxyethylene hydrogenated castor oil, polyethylene glycol, polypropylene glycol, and diethylene glycol.

Zwitterionic (amphoteric) surfactants have both cationic and anionic centers attached to the same molecule. The cationic part is based on primary, secondary, or tertiary amines or quaternary ammonium cations. The anionic part can be more variable and include sulfonates, carboxylates, and phosphate. Examples of zwitterionic surfactants include, but are not limited to, CHAPS (3-[(3-cholamidopropyl)dimethylammonio]-1-propanesulfonate), cocamidopropyl hydroxysultaine, cocamidopropyl betaine, phosphatidylethanolamine, phosphatidylcholine, sphingomyelins, lauryldimethylamine oxide, and myristamine oxide.

Other than in the working examples or where otherwise indicated, all numbers expressing amounts of materials, reaction conditions, time durations, quantified properties of materials, and so forth, stated in the specification and claims are to be understood as being modified in all instances by the term "about".

It will be understood that any numerical range recited herein includes all sub-ranges with that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

A personal care composition disclosed herein comprises a crosslinked silicone elastomer prepared by
  (1) preparing crosslinkable siloxane by reacting
    (a) α, ω-dihydroxypoly(diorganosiloxane) having a viscosity (25° C.) of about 5 to about 3000 mPa·s; and
    (b) organotrialkoxysilane with a general formula $R^1Si(OR^2)_3$;
  wherein:
  $R^1$ is a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
  $R^2$ is methyl, ethyl, or 2-methoxyethyl;
  (2) emulsifying the crosslinkable siloxane in the presence of a surfactant;
  (3) crosslinking the emulsified siloxane; and wherein the personal care composition is free of a polyether compound.

The disclosure also provides a personal care composition comprising a crosslinked silicone elastomer prepared by (1) preparing crosslinkable siloxane by reacting
  (a) α, ω-dihydroxypoly(diorganosiloxane) having a viscosity (25° C.) of about 5 to about 3000 mPa·s; and
  (b) organotrialkoxysilane with a general formula $R^1Si(OR^2)_3$;
  wherein:
  $R^1$ a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
  $R^2$ is methyl, ethyl, or 2-methoxyethyl;
  wherein the alkoxyl group of component (b) is about 1.5 to about 5 per silanol groups of component (a);
(2) emulsifying the crosslinkable siloxane in the presence of a surfactant;
(3) crosslinking the emulsified siloxane; and
wherein the personal care composition is free of a polyether compound.

The disclosure further provides a personal care composition comprising a crosslinked silicone elastomer powder that is spherical and prepared by
(1) preparing crosslinkable siloxane by reacting
  (a) α, ω-dihydroxypoly(diorganosiloxane) having a viscosity (25° C.) of about 5 to about 3000 mPa·s; and
  (b) organotrialkoxysilane with a general formula $R^1Si(OR^2)_3$;
  wherein:
  $R^1$ is a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
  $R^2$ is methyl, ethyl, or 2-methoxyethyl;
(2) emulsifying the crosslinkable siloxane in the presence of a surfactant.
(3) crosslinking the emulsified siloxane to form crosslinked silicone elastomer emulsion; and
(4) drying the crosslinked silicone elastomer emulsion to isolate solid crosslinked silicone elastomer powder;
wherein the personal care composition is free of a polyether compound.

In one aspect, the crosslinked silicone elastomer powder is spherical.

In another aspect, the crosslinked silicone elastomer powder is free of surfactant.

In some aspects, the personal care composition described above is free of a polyether compound.

I. Condensation Reaction (1) α, ω-dihydroxypoly(diorganosiloxane)

In some aspects, the α, ω-dihydroxypoly(diorganosiloxane) described above has a general formula of $HO[(R^3)_2SiO]_pH$.

In some aspects, each $R^3$ is independently a substituted or unsubstituted alkyl group, a substituted or unsubstituted alkenyl group, or a substituted or unsubstituted aryl group.

In some aspects, each $R^3$ is independently a substituted or unsubstituted alkyl group having 1 to 30 carbon atoms. In some aspects, each $R^3$ is independently a substituted or unsubstituted alkyl group having 1 to 10 carbon atoms. In some aspects, the alkyl group is methyl, ethyl, propyl, butyl, pentyl, hexyl, heptyl, octyl, nonyl, or decyl. In some aspects, each $R^3$ is methyl.

In some aspects, each $R^3$ is independently a substituted alkyl group that is a halogen substituted alkyl group. In some aspects, the halogen substituted alkyl group is 3-chloropropyl, or a 3,3,3-trifluoropropyl.

In some aspects, each $R^3$ is independently a substituted or unsubstituted alkenyl group having 2 to 8 carbon atoms. In some aspects, each $R^3$ is independently a substituted or unsubstituted alkenyl group having 2 to 4 carbon atoms. In some aspects, the alkenyl group is a vinyl group, or an allyl group.

In some aspects, each $R^3$ is independently a substituted or unsubstituted aryl group. In some aspects, the $R^3$ is a substituted aryl group that is a phenyl group substituted with an alkyl group having 1 to 4 carbon atoms.

In some aspects, when each $R^3$ is methyl, the α, ω-dihydroxypoly(diorganosiloxane) is α, ω-dihydroxypoly (dimethylsiloxane).

In some aspects, p is a value that makes the viscosity (25° C.) of α, ω-dihydroxypoly(diorganosiloxane) at about 5 to about 3000 mPa·s.

In some aspects, the α, ω-dihydroxypoly(diorganosiloxane) has a viscosity (25° C.) of about 5 to about 3000 mPa·s, about 5 to about 2900 mPa·s, about 5 to about 2800 mPa·s, about 5 to about 2700 mPa·s, about 5 to about 2600 mPa·s, about 5 to about 2500 mPa·s, about 5 to about 2400 mPa·s, about 5 to about 2300 mPa·s, about 5 to about 2200 mPa·s, about 5 to about 2100 mPa·s, about 10 to about 2000 mPa·s, about 10 to about 1900 mPa·s, about 10 to about 1800 mPa·s, about 10 to about 1700 mPa·s, about 10 to about 1600 mPa·s, about 10 to about 1500 mPa·s, about 10 to about 1400 mPa·s, about 10 to about 1300 mPa·s, about 10 to about 1200 mPa·s, about 10 to about 1100 mPa·s, about 15 to about 1000 mPa·s, about 15 to about 900 mPa·s, about 15 to about 800 mPa·s, about 15 to about 700 mPa·s, about 15 to about 600 mPa·s, about 15 to about 500 mPa·s, about 15 to about 400 mPa·s, about 15 to about 300 mPa·s, about 15 to about 200 mPa·s, about 15 to about 100 mPa·s, about 20 to about 90 mPa·s, about 20 to about 80 mPa·s, about 20 to about 70 mPa·s, about 20 to about 60 mPa·s, about 20 to about 50 mPa·s, or about 20 to about 40 mPa·s.

(2) Organotrialkoxysilane

In some aspects, the organotrialkoxysilane described above has a general formula $R^1Si(OR^2)_3$.

In some aspects, $R^1$ is a substituted or unsubstituted alkyl group, a substituted or unsubstituted alkenyl group, or a substituted or unsubstituted aryl group.

In some aspects, $R^1$ is a substituted or unsubstituted alkyl group having 1 to 30 carbon atoms. In some aspects, $R^1$ is a substituted or unsubstituted alkyl group having 1 to 10 carbon atoms. In some aspects, the alkyl group is methyl, ethyl, propyl, butyl, pentyl, hexyl, heptyl, octyl, nonyl, or decyl. In some aspects, $R^1$ is methyl.

In some aspects, $R^1$ is a substituted alkyl group that is a halogen substituted alkyl group. In some aspects, the halogen substituted alkyl group is 3-chloropropyl, or a 3,3,3-trifluoropropyl.

In some aspects, $R^1$ is a substituted or unsubstituted alkenyl group having 2 to 8 carbon atoms. In some aspects, $R^1$ is a substituted or unsubstituted alkenyl group having 2 to 4 carbon atoms. In some aspects, the alkenyl group is a vinyl group, or an allyl group.

In some aspects, $R^1$ is a substituted or unsubstituted aryl group. In some aspects, $R^1$ is a substituted aryl group that is a phenyl group substituted with an alkyl group having 1 to 4 carbon atoms. In some aspects, $R^1$ is phenyl.

In some aspects, each $R^2$ is independently a substituted or unsubstituted alkyl group.

In some aspects, each $R^2$ is independently a substituted alkyl group that is an alkoxy substituted alkyl group. In some aspects, the alkoxy substituted alkyl group is 2-methoxyethyl, 2-ethoxyethyl, 2-propoxyethyl, or 2-butoxyethyl.

In some aspects, each $R^2$ is independently an unsubstituted alkyl group that is methyl, ethyl, propyl, butyl, pentyl, or hexyl. In some aspects, each $R^2$ is methyl. In some aspects, each $R^2$ is ethyl. In some aspects, each $R^2$ is propyl.

In some aspects, the organotrialkoxysilane is methyltrimethoxysilane, methyltriethoxysilane, methyltri-n-propoxysilane, phenyltrimethoxysilane, or phenyltriethoxysilane.

In some aspects, the alkoxyl group (—$OR^2$) of component (b) is about 1.5 to about 5 per silanol groups (—$(R^3)_2SiO$—) of component (a), about 2 to about 4.5 per silanol groups of component (a), about 2.5 to about 4 per silanol groups of component (a), or about 3 to about 3.5 per silanol groups of component (a).

(3) Catalysts Used in the Condensation Reaction

The disclosure further provides that the condensation reaction between component (a) and component (b) is performed with a catalyst. Examples of the catalyst for the condensation reaction include amines, ammonium salts, ammonium hydroxides, phosphonium hydroxides, and combinations thereof.

Examples of amines as the catalyst for the condensation reaction include, but are not limited to, monomethylamine, dimethylamine, monoethylamine, diethylamine, ethylenediamine, hexamethylenetetramine, and their silanolate compounds including α-aminopropyltriethoxysilane.

Examples of ammonium salts as the catalyst for the condensation reaction include, but are not limited, to (1-butyl)triethylammonium bromide, (1-decyl)trimethylammonium bromide, (1-dodecyl)trimethylammonium bromide, (1-dodecyl)trimethylammonium chloride, benzalkonium chloride, and their silanolate compounds including trimethyl [3-(triethoxysilyl)propyl]ammonium chloride.

Examples of ammonium hydroxides as the catalyst for the condensation reaction include, but are not limited to, tetramethylammonium hydroxide, dimethylbenzylammonium hydroxide, and their silanolate compounds including trimethyl[3-(triethoxysilyl)propyl]ammonium hydroxide.

Examples of phosphonium hydroxides as the catalyst for the condensation reaction include, but are not limited to, tetramethylphosphonium hydroxide, tetra-n-butylphosphonium hydroxide, phenyltrimethylphosphonium hydroxide, tetramethylphosphonium methoxide, tetrabutylphosphonium butoxide, butyltricyclohexylphosphonium hydroxide, and their silanolate compounds including trimethyl[3-(triethoxysilyl)propyl]phosphonium hydroxide.

In some aspects, the catalyst for the condensation reaction is ammonium hydroxides, or their silanolate compounds. In some aspects, the catalyst for the condensation reaction is tetramethylammonium hydroxide. In some aspects, the catalyst for the condensation reaction are phosphonium hydroxide, or their silanolate compounds.

In some aspects, the amount of the catalyst for the condensation reaction is about 0.001 to about 0.1 parts by weight with respect to about 100 parts by weight of the total amount of component (a) and component (b), about 0.002 to about 0.09 parts by weight, about 0.003 to about 0.08 parts by weight, about 0.004 to about 0.07 parts by weight, about 0.005 to about 0.06 parts by weight, about 0.006 to about 0.05 parts by weight, about 0.007 to about 0.04 parts by weight, about 0.008 to about 0.03 parts by weight, about 0.009 to about 0.02 parts by weight, or about 0.01 to about 0.02 parts by weight.

(4) Crosslinkable Siloxane

In some aspects, the crosslinkable siloxane has a viscosity (25° C.) of about 5 to about 10000 mPa·s, about 6 to about 9000 mPa·s, about 7 to about 8000 mPa·s, about 8 to about 7000 mPa·s, about 9 to about 6000 mPa·s, or about 10 to about 5000 mPa·s.

In addition, a filler may be added as an optional component to the crosslinkable polyorganosiloxane in order to control its fluidity and to improve the mechanical strength of the obtained crosslinked silicone elastomer fine particles. Such fillers include, but are not limited to, reinforcing fillers such as precipitated silica, fumed silica, pyrogenic silica, fumed Titanium Oxide, ground quartz, and diatomaceous earth, non-reinforcing fillers such as aluminosilicate, iron oxide, Zinc Oxide, and calcium carbonate, and fillers obtained by treating these surfaces with organosilicon compounds such as hexamethylsilazane, trimethylchlorosilane, polydimethylsiloxane, and polymethylhydrogensiloxane.

II. Emulsification Process

In some aspects, one or more surfactant is added into the reaction product of component (a) and component (b) to form an emulsion. In some aspects, the one or more surfactant is selected from the group consisting of an anionic surfactant, a cationic surfactant, a nonionic surfactant, a zwitterionic surfactants, and combinations thereof.

Examples of anionic surfactants include, but are not limited to, hexyl benzene sulfonic acid, octyl benzene sulfonic acid, tetradecene sulfonic acid, hexadecyl sulfonic acid, hydroxydodecane sulfonic acid, hydroxytetradecane sulfonic acid, lauryl sulfate, lauryl polyoxyethylene ether sulfate, and their salts thereof.

Examples of cationic surfactants include, but are not limited to, octyltrimethylammonium hydroxide, lauryltrimethylammonium hydroxide, stearyltrimethylammonium hydroxide, lauryltrimethylammonium chloride, stearyltrimethylammonium chloride, cetyltrimethylammonium chloride, benzalkonium chloride, and stearyldimethylbenzylammonium chloride.

Examples of nonionic surfactants include, but are not limited to, polyoxyethylene lauryl ether, polyoxyethylene fatty acid ester, polyoxyethylene sorbitan fatty acid ester, sorbitan fatty acid ester, polyoxyethylene hydrogenated castor oil, polyethylene glycol, polypropylene glycol, and diethylene glycol.

Examples of zwitterionic (amphoteric) surfactants include, but are not limited to, CHAPS (3-[(3-cholamidopropyl)dimethylammonio]-1-propanesulfonate), cocamidopropyl hydroxysultaine, cocamidopropyl betaine, phosphatidylcholine, lauryldimethylamine oxide, and myristamine oxide.

In some aspects, the surfactant is sodium lauryl sulfate.

In some aspects, the surfactant is sodium lauryl polyoxyethylene ether sulfate.

In some aspects, the amount of the total amount of surfactant used is about 0.05 to about 50 parts by weight based on about 100 parts by weight of the crosslinkable polyorganosiloxane, about 0.06 to about 40 parts by weight, about 0.07 to about 30 parts by weight, about 0.08 to about 20 parts by weight, about 0.09 to about 10 parts by weight, about 0.1 to about 10 parts by weight, about 0.2 to about 9 parts by weight, about 0.3 to about 8 parts by weight, about 0.4 to about 7 parts by weight, about 0.5 to about 6 parts by weight, about 0.6 to about 5 parts by weight, about 0.7 to about 4 parts by weight, about 0.8 to about 3 parts by weight, about 0.9 to about 2 parts by weight, or about 1 to about 1.5 parts by weight.

III. Crosslinking Reaction

In some aspects, one or more acid is added as a catalyst in the emulsion to crosslink the reaction product of component (a) and component (b) to form a crosslinked silicone elastomer.

In some aspects, the one or more acid includes inorganic acids, organic acids, or combinations thereof.

Examples of inorganic acids include, but are not limited to, hydrochloric acid, sulfuric acid, nitric acid, phosphoric acid, and sulfamic acid. Examples of organic acids include, but are not limited to, formic acid, citric acid, acetic acid, and p-toluenesulfonic acid.

In some aspects, the amount of these acids used is about 0.05 to about 10 parts by weight based on about 100 parts by weight of the crosslinkable polyorganosiloxane, about 0.1 to about 10 parts by weight, about 0.5 to about 9.5 parts by weight, about 1 to about 9.5 parts by weight, about 1.5 to about 9 parts by weight, about 2 to about 9 parts by weight, about 2.5 to about 8.5 parts by weight, about 3 to about 8.5 parts by weight, about 3.5 to about 8 parts by weight, about 4 to about 8 parts by weight, about 4.5 to about 7.5 parts by weight, or about 5 to about 7 parts by weight.

IV. Drying Crosslinked Silicone Elastomer

In some aspects, one or more salts are added to separate the crosslinked silicone elastomer from the emulsion. In some aspects, isopropanol is added to separate the crosslinked silicone elastomer from the emulsion. In some aspects, the salt is calcium chloride. In some aspects, the amount of salts used is about 0.01 to about 1 parts by weight with respect to about 100 parts by weight of the emulsion, about 0.05 to about 0.9 parts by weight, about 0.1 to about 0.8 parts by weight, about 0.2 to about 0.7 parts by weight, about 0.3 to about 0.6 parts by weight, or about 0.4 to about 0.5 parts by weight. In some aspects, the amount of isopropanol used is about 5 to about 20 parts by weight with respect to about 100 parts by weight of the emulsion, about 6 to about 20 parts by weight, about 7 to about 19 parts by weight, about 8 to about 19 parts by weight, about 9 to about 18 parts by weight, about 10 to about 18 parts by weight, about 11 to about 17 parts by weight, about 12 to about 17 parts by weight, about 13 to about 16 parts by weight, or about 14 to about 16 parts by weight. In some ascpects, the crosslinked silicone elastomer is filtered and dried to form a crosslinked silicone elastomer powder. In some ascpects, the crosslinked silicone elastomer powder is free of surfactants.

V. Ingredients in Personal Care Compositions

In one aspect, the personal care composition comprises a crosslinked silicone elastomer. In another aspect, the personal care composition comprises a crosslinked silicone elastomer powder.

In some aspects, the personal care composition further comprises one or more volatile and non-volatile oils selected from the group consisting of hydrocarbon, silicone, fluorinated oils, and combinations thereof.

In some aspects, the oils are selected from the group consisting of dimethicone, caprylyl methicone, phenyl modified silicone, alkanes from 7 to 17 carbon atoms, fatty acid esters, and combinations thereof. In some aspects, the alkane is linear or branched nonane, linear or branched decane, linear or branched undecane, linear or branched dodecane, linear or branched tridecane, linear or branched isododecane, linear or branched squalene, linear or branched hemisqualane, or combinations thereof.

In some aspects, the personal care composition further comprises an aqueous phase. In some aspects, the aqueous phase comprises one or more of water, glycerin, butylene glycol, propanediol, xanthan gum, steareth 21, sodium polyacrylate, disodium EDTA, and sodium chloride.

In some aspects, the personal care composition further comprises one or more organic or inorganic sunscreens. In some aspects, the sunscreens are selected from the group consisting of titanium dioxide, zinc oxide, oxybenzone, ethylhexyl salicylate, homosalate, avobenzone, octocrylene, and combinations thereof.

In some aspects, the personal care composition further comprises one or more film formers. In some aspects, the one or more film former is a silicone resin selected from the group consisting of MQ resin, MT resin, T-propyl resin, and combinations thereof. In some aspects, the one or more film former is selected from the group consisting of acrylates/polytrimethylsiloxy-methacrylate copolymer, acrylates/dimethicone copolymer, vinylpyrrolidone/eicosene copolymer, styrene/acrylates copolymer, and combinations thereof.

In some aspects, the personal care composition further comprises one or more waxes. In some aspects, the wax is selected from the group consisting of $C_{30-45}$ alkyl dimethicone, $C_{30-45}$ alkyl cetearyl dimethicone crosspolymer, beeswax, ozokerite wax, carnauba wax, shea butter, stearic acid, cetyl alcohol, and combinations thereof.

In some aspects, the personal care composition further comprises one or more emulsifiers. In some aspects, the one or more emulsifier is polyglyceryl-4 diisostearate/polyhydroxystearate/sebacate.

In some aspects, the personal care composition further comprises one or more of particulates, pigments and dyes. In some aspects, the particulates are selected from the group consisting of silica, talc, aluminum starch octenylsuccinate, polymethylsilsesquioxane, nylon-12, starch particles including tapioca starch and rice starch, cellulose particles, cellulose acetate particles, titanium dioxide, boron nitride, mica, organo-modified hectorite clay, and combinations thereof. In some aspects, the pigment is iron oxide or lake pigments. In some aspects, the dye is Phoxine B.

In some aspects, the personal care composition further comprises one or more preservatives. In some aspects, the preservative is phenoxy ethanol.

In some aspects, the personal care composition is a deodorant, an antiperspirant, a skin cream, a facial cream, a hair shampoo, a hair conditioner, a mousse, a hair styling gel, a hair spray, a protective cream, a lipstick, a lip color, a facial foundations, blushes, makeup, mascara, a skin care lotion, a moisturizer, a facial treatment, eye serum, eye cream, a personal cleanser, a facial cleanser, a bath oil, a perfume, a shaving cream, a pre-shave lotion, an after-shave lotion, a cologne, a sachet, loose facial powder, compact powder, eye shadow, and a sunscreen.

Example 1

Preparation of Emulsion 1

Preparation of reactive oil: 427 parts of α, ω-dihydroxypoly (dimethylsiloxane) having a viscosity of 85 mPa·s and 42 parts of methyltriethoxysilane were charged into a 500 mL flask equipped with a reflux stirrer. The reactants were stirred and mixed. The temperature was raised to 100° C. While stirring, 0.015 part of a 30% aqueous solution of tetramethylammonium hydroxide as a catalyst was added. When the reaction continued for 5 hours, ethanol produced by the condensation reaction was brought to a reflux state, and the temperature in the flask became 94° C. Thereafter, the temperature was raised to 140° C., and the reaction continued for 2 hours to remove the produced ethanol and to decompose the catalyst tetramethylammonium hydroxide. Subsequently, the compounds with low boiling point were removed under heating at 140° C. and reduced pressure of 2.6 kPa. After 3 hours. The reaction was cooled to room temperature to obtain 445 parts of reactive oil having a viscosity of 470 mPa·s.

Preparation of emulsion of silicone elastomer particles: 4.2 parts of sodium lauryl sulfate was dissolved in 90 parts of ion-exchanged water. Next, 300 parts of reactive oil was added and stirred for 5 minutes. Next, 150 parts of ion-exchanged water was added dropwise over 5 minutes while stirring continued. Then the mixture was uniformly emulsified with a colloid mill. Next, the obtained emulsion was transferred to a flask, and 6 parts of 20% sulfuric acid was added with stirring. The reaction continued at 50° C. for 17 hours with stirring. After cooling to 30° C. with stirring, the reaction was stopped by dripping triethanolamine until pH reached 7. The aqueous dispersion of silicone elastomer fine particles (hereinafter referred to "Emulsion 1") was obtained. The volume average particle diameter of the crosslinked silicone elastomer in Emulsion 1 was 5.7 m.

Example 2

Preparation of Emulsion 2

Preparation of reactive oil: 314 parts of α, ω-dihydroxypoly (dimethylsiloxane) having a viscosity of 30 mPa·s and 146 parts of methyltriethoxysilane were charged into a 500 mL flask equipped with a reflux stirrer. The reactants were stirred and mixed. The temperature was raised to 100° C. While stirring, 0.015 part of a 30% aqueous solution of tetramethylammonium hydroxide as a catalyst was added. When the reaction continued for 4 hours, ethanol produced by the condensation reaction was brought to a reflux state, and the temperature in the flask became 87° C. Next, the temperature was raised to 140° C., and the reaction continued for 2 hours to remove the produced ethanol and to decompose the catalyst tetramethylammonium hydroxide. Thereafter, the compounds with low boiling point were removed under heating at 140° C. and reduced pressure of 2.6 kPa. After 3 hours, the reaction was cooled to room temperature to obtain 348 parts of reactive oil having a viscosity of 104 mPa·s.

Preparation of emulsion of silicone elastomer particles: 1.2 parts of sodium polyoxyethylene lauryl ether sulfate was dissolved in 90 parts of ion-exchanged water. Next, 300 parts of reactive oil was added and stirred for 5 minutes. Next, 150 parts of ion-exchanged water was added dropwise over 5 minutes while stirring continued. The mixture was uniformly emulsified with a colloid mill. Next, the obtained emulsion was transferred to a flask, and 6 parts of 20% sulfuric acid was added with stirring. The reaction continued at 50° C. for 20 hours with stirring. Then, during stirring, a solution prepared by mixing a 10% sodium carbonate solution and a 30% polyoxyethylene sodium lauryl ether sulfate solution at a weight ratio of 1:1 was added dropwise into the reaction until the pH reached 7. The aqueous dispersion of silicone elastomer fine particles (hereinafter referred to "Emulsion 2") was obtained. The volume average particle diameter of the crosslinked silicone elastomer in the Emulsion 2 was 7.4 m.

Example 3

Preparation of Dried Crosslinked Silicone Elastomer Powder 1

100 g of Emulsion 2 was charged into a 4-neck flask with overhead stirrer, a thermocouple, a nitrogen line, and a condenser. The emulsion was stirred at 200 rpm at room temperature. Then 2 g of 10 wt % $CaCl_2$) solution and 15 g isopropanol were added to the flask. After stirring for 1 hour, the mixture was filterred, and the residue was washed with 100 g deionized water at 50° C. The washing step was repeated for three times to remove residual impurities. Then the silicone elastomer residues were dried at 100° C. under vacuum to achieve silicone elastomer in white powder form. % Solids on the powder were measured by placing 1 g sample at 150° C. in convection oven. Residual surfactants were measured by UV/Vis spectroscopic method. Table 1 lists the analysis of the products.

TABLE 1

| Property | Crosslinked Silicone Elastomer Powder 1 | Crosslinked Silicone Elastomer Powder 2 | Crosslinked Silicone Elastomer Powder 3 | Crosslinked Silicone Elastomer Powder 4 |
| --- | --- | --- | --- | --- |
| Solids % | 99.8 | 99.3 | 99.1 | 99.4 |
| Surfactant % | 0.008 | 0.06 | 0.79 | 0.007 |
| Powder agglomeration | No | No | Yes | No |
| Viscosity (cP. 19% in D5) | 125500 | 120400 | 25600 | 12000 |
| Appearance of swollen gel | Gel | Gel | Liquid | Liquid |
| Application on skin | Smooth | Smooth | Agglomerate | Agglomerate |

Example 4

Preparation of Dried Crosslinked Silicone Elastomer Powder 2

100 kg of Emulsion 2 and 2 kg of 10 wt % $CaCl_2$) solution were charged into the kettle. The emulsion was sirred at room temperature for 30 mins, and left for 12 hours without stirring. Then the emulsion was stirred again. After 30 mins, the contents were filtered by centrifuge, and the residues were washed with 100 kg of water while centrifuging, leaving a wet cake with 76% solids. The wet cake was dried in a rotary dryer at 110° C. for 24 hours, and it was further died at 120° C. for 12 hours. Table 1 lists the analysis of the dried powder.

Example 5

Preparation of Dried Crosslinked Silicone Elastomer Powder 3

The emulsion of the invention can be dried into a powder by spray drying. 100 kg of the Emulsion 2 was dried by spray drying with 1.0 mm 2-fluid nozzle with nitrogen gas and at pressure of 2.0 bar. The inlet temperature of gas was 225° C. The feed rate was 1.9 kg/hr based upon the dried powder. Table 1 lists the analysis of the dried powder.

Example 6

Preparation of Dried Crosslinked Silicone Elastomer Powder 4

360 kg of Emulsion 2 and 7.2 kg of 10 wt % $CaCl_2$) solution were charged into the kettle. The emulsion was stirred for 30 mins, and left for 12 hours without stirring. Then the emulsion was stirred again. After 30 mins, the contents were filtered by centrifuge, and the residues were washed with 900 kg of water while centrifuging, leaving a wet cake with 88% solids. The wet cake was dried in a box dryer with 1.5 kg of wet cake in each tray at 105° C. for 22 hrs. Table 1 lists the analysis of the dried powder.

Example 7

Preparation of Personal Care Formulation 1

Table 2 lists the ingredients of Personal Care Formulation 1 (water-in-oil skin primer). The procedure for preparing Personal Care Formulation 1 is described as following. Phase A ingredients were combined with a disperser. The mixture was stirred at 70° C. for 20 mins until it was homogeneous. Phase B ingredients were combined with a disperser. The mixture was stirred at 70° C. until it was homogeneous. Then phase B was added to phase A. The mixture was stirred at 70° C. until it was homogeneous. Phase C ingredients were combined with a disperser. The mixture was stirred at 70° C. until it was homogeneous. Then phase C was slowly added to phases A and B at 70° C. while stirring at 300 rpm. The mixture was stirred to be emulsified for 20 mins at 300 rpm and 70° C. Then the emulsion was cooled to room temperature. Next, phase D was added into the emulsion. The emuslion was stirred at 300 rpm for 10 mins or 2000 rpm for 3 mins until it was homogeneous.

TABLE 2

| Phase | Ingredient | % w/w |
|---|---|---|
| A | Caprylyl Methicone | 3.50 |
|  | Ethylhexyl Methoxycinnamate | 5.00 |
|  | Trimethylsiloxysilicate | 2.00 |
|  | Dimethicone | 5.28 |
|  | Crosslinked Silicone Elastomer Powder 1 | 0.72 |
|  | Sorbitan Sesquiisostearate | 0.50 |
|  | Polyglyceryl-4 Diisostearate/Polyhydroxystearate/Sebacate | 4.00 |
| B | Caprylyl Methicone | 5.00 |
|  | Silica | 5.00 |
|  | Hydrogen Dimethicone; Zinc Oxide | 1.50 |
|  | Hydrogen Dimethicone; Titanium Dioxide; Aluminum Hydroxide | 1.50 |
|  | Methicone; Iron Oxide (CI 77492) | 0.05 |
|  | Methicone; Iron Oxide (CI 77491) | 0.05 |
|  | Methicone; Iron Oxide (CI 77499) | 0.015 |
| C | Aqua | q.s. 100 |
|  | Glycerin | 5.00 |
|  | Polysorbate 20 | 0.50 |
|  | Sodium Chloride | 1.00 |
| D | Phenoxy ethanol | 0.50 |

Example 8

Preparation of Personal Care Formulation 2

Table 3 lists the ingredients of Personal Care Formulation 2 (water-in-silicone liquid foundation). The procedure for preparing Personal Care Formulation 2 is described as following. Phase A ingredients were combined with a disperser. The mixture was stirred at 70° C. until it was homogeneous. Phase B ingredients were combined with a disperser. The mixture was stirred at 70° C. until it was homogeneous. Then phase B was added to phase A. The mixture was stirred at 70° C. for 30 mins until it was homogeneous. Phase C ingredients were combined with a disperser. The mixture was stirred at 70° C. until it was homogeneous. Then phase C was slowly added to phases A and B at 70° C. while stirring at 300 rpm. The mixture was stirred to be emulsified for 20 mins at 300 rpm and 70° C. Then the emulsion was cooled to room temperature. Next, phase D was added into the emulsion. The emuslion was stirred at 2000 rpm for 5 mins until it was homogeneous.

Figure 1:
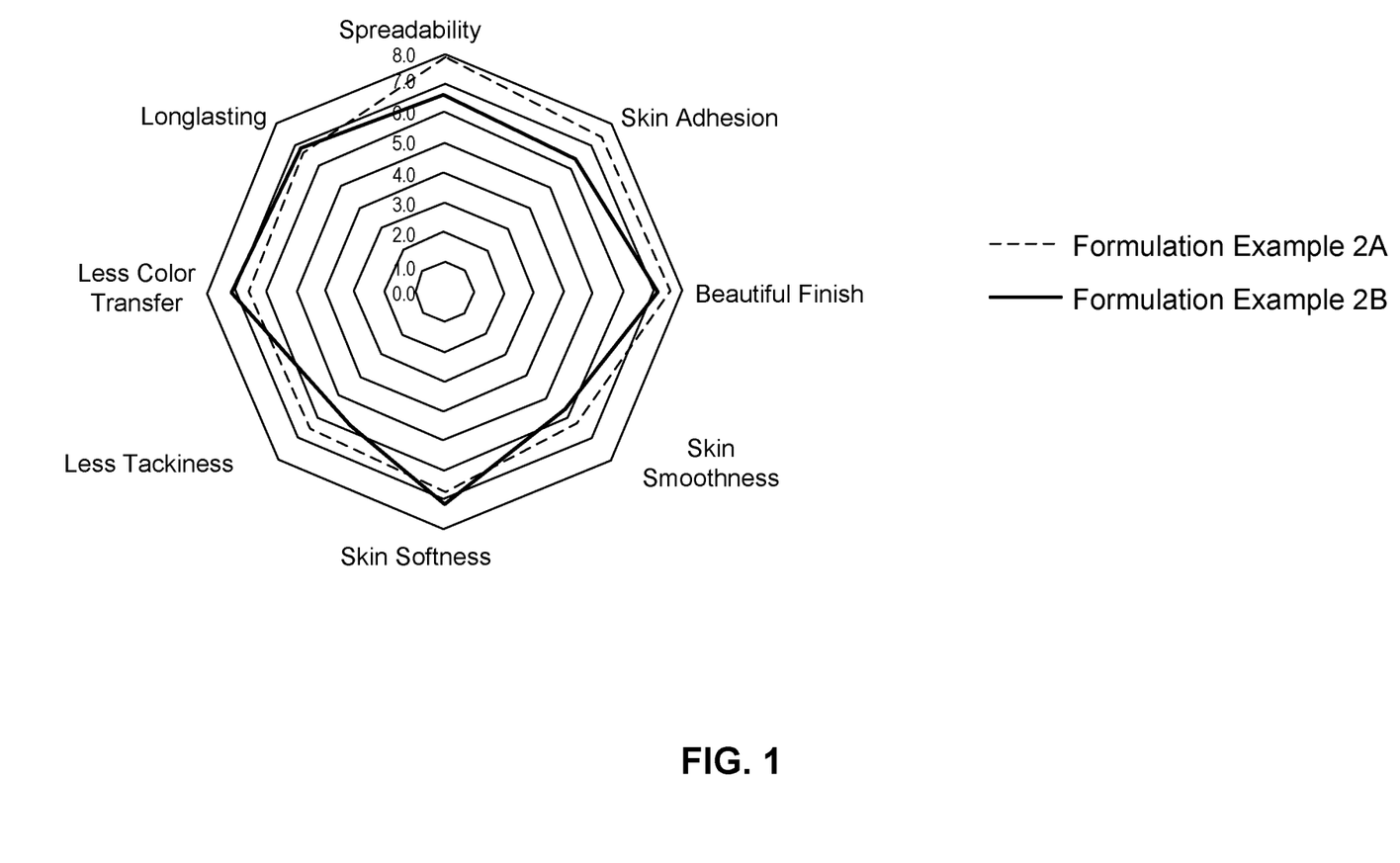
FIG. 1 describes a sensory panel study for Formulation Examples 2A and 2B.

FIG. 1 shows a sensory panel study for Formulation examples 2A and 2B. In this study, Formulation example 2A shows better spreadability, skin adhesion, smoothness and less tackiness compared to benchmark Formulation example 2B.

TABLE 3

| Phase | Ingredient | Example 2A % w/w | Example 2B % w/w |
|---|---|---|---|
| A | Caprylyl Methicone | 4.00 | 4.00 |
|  | Diphenyl Dimethicone | 5.00 | 5.00 |
|  | Polymethylsilsesquioxane | 2.00 | 2.00 |
|  | Dimethicone | 5.28 |  |
|  | Crosslinked Silicone Elastomer Powder 1 | 0.72 |  |
|  | Dimethicone; Dimethicone/Vinyl Dimethicone Crosspolymer |  | 6 |
|  | Polyglyceryl-4 Diisostearate/Polyhydroxystearate/Sebacate | 5.00 | 5.00 |
| B | Caprylyl Methicone | 7.00 | 7.00 |
|  | Silica | 5.00 | 5.00 |
|  | Hydrogen Dimethicone; Titanium Dioxide; Aluminum Hydroxide | 4.50 | 4.50 |
|  | Methicone; Iron Oxide (CI 77492) | 0.28 | 0.28 |
|  | Methicone; Iron Oxide (CI 77491) | 0.18 | 0.18 |
|  | Methicone; Iron Oxide (CI 77499) | 0.05 | 0.05 |
| C | water | 54.49 | 54.49 |
|  | Glycerin | 5.00 | 5.00 |
|  | Sodium Chloride | 1.00 | 1.00 |
| D | Phenoxy ethanol | 0.50 | 0.50 |

Example 9

Preparation of Personal Care Formulation 3

Table 4 lists the ingredients of Personal Care Formulation 3 (oil-in-water sunscreen SPF 10). The procedure for preparing Personal Care Formulation 3 is described as following. Phase B ingredients were combined and mixed at 70° C. until the mixture was homogeneous. Phase C ingredients were combined and mixed at 70° C. until the mixture was homogeneous. Phase B was added to phase C while stirring at 70° C. The mixture was stirred at 70° C. until it was homogeneous. Phase A ingredients were combined and mixed at 50° C. until the mixture was homogeneous. Then the mixture of phases B and C was added to phase A while stirring at 50° C. The mixture was stirred at 50° C. until it was homogeneous. Then the mixture was cooled to 40° C.

Next, phase D was added into the mixture. The mixture was stirred at 11,000 rpm for 1 mins until it was homogeneous.

TABLE 4

| Phase | Ingredient | % w/w |
|---|---|---|
| A | Aqua (Water) | q.s. 100 |
|  | Disodium EDTA | 0.10 |
|  | Propanediol | 2.00 |
|  | Xanthan gum | 0.30 |
|  | Glycerin | 3.00 |
| B | Cetyl alcohol | 2.50 |
|  | Glyceryl stearate | 2.50 |
|  | Glyceryl stearate; | 4.00 |
|  | Ethylhexyl salicylate | 5.00 |
|  | Homosalate | 10.00 |
|  | Avobenzone | 3.00 |
|  | Octocrylene | 2.70 |
| C | C12-15 alkyl benzoate | 5.00 |
|  | Caprylyl methicone | 5.00 |
|  | Crosslinked Silicone Elastomer Powder 2 | 5.00 |
| D | Phenoxyethanol | 1.00 |

Example 10

Preparation of Personal Care Formulation 4

Table 5 lists the ingredients of Personal Care Formulation 4 (anhydrous sunscreen). The procedure for preparing Personal Care Formulation 4 is described as following. Phase A ingredients were mixed at room temperature. Phase B ingredients were added to phase A under homogenization at 6000 rpm for 5 mins at room temperature.

TABLE 5

| Phase | Ingredients | % w/w |
|---|---|---|
| A | C9-12 alkane | 18.00 |
|  | Caprylyl Methicone | 18.00 |
|  | Methyl Trimethicone | 36.00 |
| B | Zinc Oxide; Triethoxycaprylyl Silane | 14.00 |
|  | Crosslinked Silicone Elastomer Powder 1 | 14.00 |

Example 11

Preparation of Personal Care Formulation 5

Table 6 lists the ingredients of Personal Care Formulation 5 (lipstick). The procedure for preparing Personal Care Formulation 5 is described as following. Phase A ingredients were combined and mixed at 70° C. until the mixture was homogeneous. Phase B ingredients were combined and mixed at 70° C. until the mixture was homogeneous. Then phase B was added to phase A while stirring. The mixture was stirred at 70° C. until it was homogeneous. Then the mixture as cooled to room temperature.

TABLE 6

| Phase | Ingredients | % w/w |
|---|---|---|
| A | Butylated Hydroxytoluene | 0.10 |
|  | Cyclopentasiloxane; Trimethylsiloxysilicate | 5.00 |
|  | Beeswax | 3.00 |
|  | Ozokerite wax | 5.00 |
|  | Carnauba wax | 4.00 |
|  | C30-45 Alkyl Dimethicone Crosspolymer | 5.00 |
|  | Dimethicone; Cetearyl Dimethicone Crosspolymer; C30-45 Alkyl Dimethicone; Beeswax | 4.00 |
|  | shea butter | 7.00 |

TABLE 6-continued

| Phase | Ingredients | % w/w |
|---|---|---|
|  | Cetyl alcohol | 0.80 |
|  | Silica | 2.00 |
|  | Caprylic/Capric Triglyceride | 2.00 |
|  | Isopropyl Myristate | 12.1 |
|  | Polyglyceryl-2 Triisostearate; Red 28 AL Lake (pigment) | 2.11 |
|  | Polyglyceryl-2 Triisostearate; Red Iron Oxide | 5.26 |
|  | Phoxine B (dye) | 2.63 |
| B | Dimethicone | 10.00 |
|  | Isododecane | 10.00 |
|  | Castor oil | 10.00 |
|  | Crosslinked Silicone Elastomer Powder 2 | 10.00 |

Example 12

Preparation of Personal Care Formulation 6

Table 7 lists the ingredients of Personal Care Formulation 6 (ultra smooth skin clarifying facial serum). The procedure for preparing Personal Care Formulation 6 is described as following. Phase B ingredients were combined and mixed at 70° C. until the mixture was homogeneous. Phase C ingredients were combined and mixed at 70° C. until the mixture was homogeneous. Phase B was added to phase C while stirring at 70° C. The mixture was stirred at 70° C. until it was homogeneous. Phase A ingredients were combined and mixed at 50° C. until the mixture was homogeneous. Then the mixture of phases B and C was added to phase A while stirring at 50° C. The mixture was stirred at 50° C. until it was homogeneous. Then the mixture was cooled to 40° C. Next, phase D was added into the mixture. The mixture was stirred until it was homogeneous. Then the mixture as cooled to room temperature.

Figure 2:
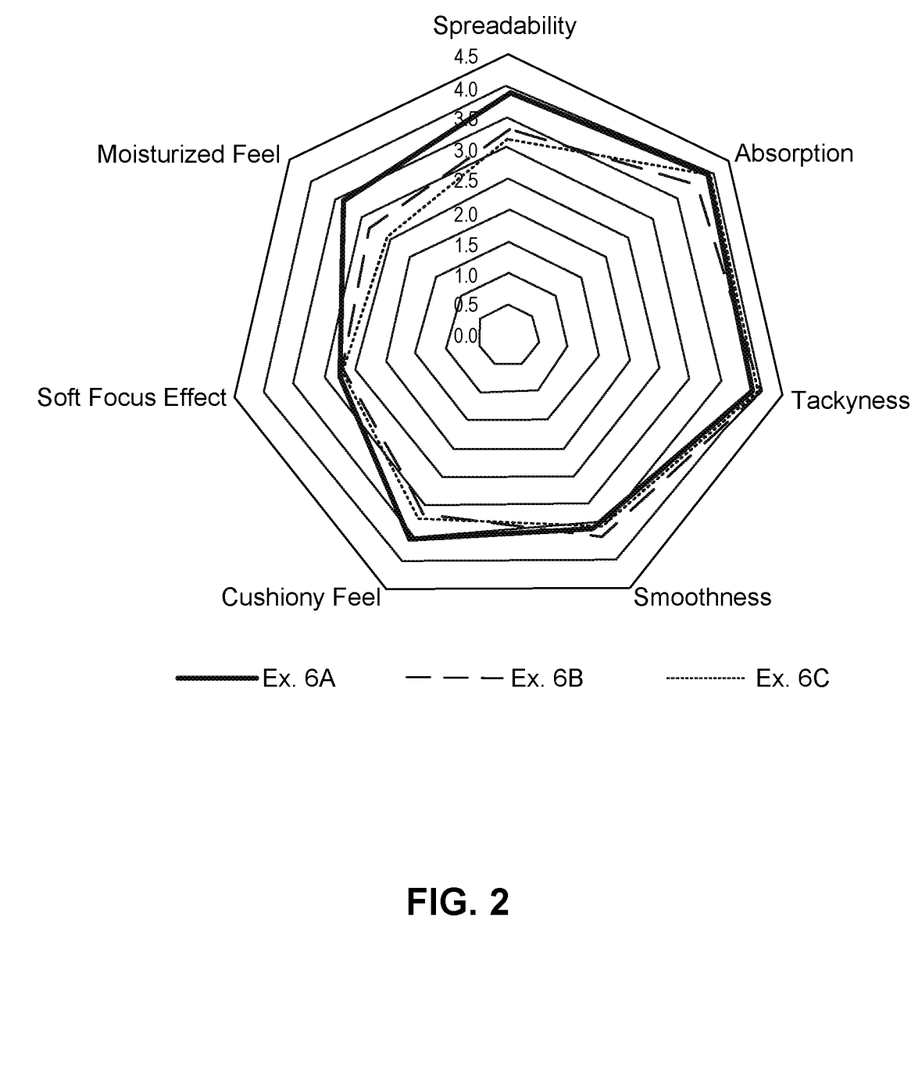
FIG. 2 describes a sensory panel study for Formulation Examples 6A, 6B, and 6C.

FIG. 2 shows a sensory panel study for Formulation examples 6A, 6B, and 6C. In this study, Formulation example 6A shows better spreadability, cushiony feel, and moisturized feel compared to benchmark Formulation examples 6B and 6C.

TABLE 7

| Phase | Trade Name | Example 6A % w/w | Example 6B % w/w | Example 6C % w/w |
|---|---|---|---|---|
| A | Water | 62.45 | 62.45 | 62.45 |
|  | Glycerin | 5.00 | 5.00 | 5.00 |
|  | Sodium Polyacrylate | 0.50 | 0.50 | 0.50 |
|  | Steareth 21 | 2.00 | 2.00 | 2.00 |
| B | Caprylic/Capric Triglyceride | 7.00 | 7.00 | 7.00 |
|  | Hemisqualane | 5.00 | 5.00 | 5.00 |
|  | Cetostearyl alcohol | 2.00 | 2.00 | 2.00 |
|  | Steareth 2 | 0.50 | 0.50 | 0.50 |
| C | Caprylyl Methicone | 5.00 | 5.00 | 5.00 |
|  | Crosslinked Silicone Elastomer Powder 1 | 10.00 |  |  |
|  | Polysilicone-11; Laureth-12 |  |  | 10.00 |
|  | Dimethicone/Vinyl Dimethicone Crosspolymer |  | 10.00 |  |
| D | Hyalurosmooth PW LS 8997 | 0.05 | 0.05 | 0.05 |
|  | Preservative | 0.5 | 0.5 | 0.5 |

What is claimed is:

1. A personal care composition comprising a crosslinked silicone elastomer prepared by
   (1) preparing crosslinkable siloxane by reacting
      (a) α, ω-dihydroxypoly(diorganosiloxane) having a viscosity of about 5 to about 3000 mPa·s (25° C.); and
      (b) organotrialkoxysilane with a general formula $R^1Si(OR^2)_3$;

wherein:
R¹ is a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
R² is methyl, ethyl, or 2-methoxyethyl;
(2) emulsifying the crosslinkable siloxane in the presence of a surfactant; and
(3) crosslinking the emulsified siloxane;
wherein the personal care composition is free of a polyether compound.

2. The personal care composition of claim 1, wherein the personal care composition further comprises one or more volatile and non-volatile oils selected from the group consisting of hydrocarbon, silicone, fluorinated oils, and combinations thereof.

3. The personal care composition of claim 2, wherein the oils are selected from the group consisting of dimethicone, caprylyl methicone, phenyl modified silicone, alkanes from 7 to 17 carbon atoms, fatty acid esters, and combinations thereof.

4. The personal care composition of claim 3, wherein the alkane is linear or branched nonane, linear or branched decane, linear or branched undecane, linear or branched dodecane, linear or branched tridecane, linear or branched isododecane, linear or branched squalene, linear or branched hemisqualane, or combinations thereof.

5. The personal care composition of claim 1, wherein the personal care composition further comprises an aqueous phase.

6. The personal care composition of claim 5, wherein the aqueous phase comprises one or more of water, glycerin, butylene glycol, propanediol, xanthan gum, steareth 21, sodium polyacrylate, disodium EDTA, and sodium chloride.

7. The personal care composition of claim 1, wherein the personal care composition further comprises one or more organic or inorganic sunscreens.

8. The personal care composition of claim 7, wherein the sunscreens are selected from the group consisting of titanium dioxide, zinc oxide, oxybenzone, ethylhexyl salicylate, homosalate, avobenzone, octocrylene, and combinations thereof.

9. The personal care composition of claim 1, wherein the personal care composition further comprises one or more film formers.

10. The personal care composition of claim 9, wherein the one or more film former is a silicone resin selected from the group consisting of MQ resin, MT resin, T-propyl resin, and combinations thereof.

11. The personal care composition of claim 9, wherein the one or more film former is selected from the group consisting of acrylates/polytrimethylsiloxy-methacrylate copolymer, acrylates/dimethicone copolymer, vinylpyrrolidone/eicosene copolymer, styrene/acrylates copolymer, and combinations thereof.

12. The personal care composition of claim 1, wherein the personal care composition further comprises one or more waxes.

13. The personal care composition of claim 12, wherein the wax is selected from the group consisting of $C_{30-45}$ alkyl dimethicone, $C_{30-45}$ alkyl cetearyl dimethicone crosspolymer, beeswax, ozokerite wax, carnauba wax, shea butter, stearic acid, cetyl alcohol, and combinations thereof.

14. The personal care composition of claim 1, wherein the personal care composition further comprises one or more emulsifiers.

15. The personal care composition of claim 1, wherein the personal care composition further comprises one or more of particulates, pigments and dyes.

16. The personal care composition of claim 15, wherein the particulates are selected from the group consisting of silica, talc, aluminum starch octenylsuccinate, polymethylsilsesquioxane, nylon-12, starch particles including tapioca starch and rice starch, cellulose particles, cellulose acetate particles, titanium dioxide, boron nitride, mica, organo-modified hectorite clay, and combinations thereof.

17. The personal care composition of claim 1, wherein the personal care composition further comprises one or more preservatives.

18. The personal care composition of claim 1, wherein the personal care composition is a deodorant, an antiperspirant, a skin cream, a facial cream, a hair shampoo, a hair conditioner, a mousse, a hair styling gel, a hair spray, a protective cream, a lipstick, a lip color, a facial foundation, blushes, makeup, a mascara, a skin care lotion, a moisturizer, a facial treatment, eye serum, eye cream, a personal cleanser, a facial cleanser, a bath oil, a perfume, a shaving cream, a pre-shave lotion, an after-shave lotion, a cologne, a sachet, loose facial powder, compact powder, eye shadow, or a sunscreen.

19. A personal care composition comprising a crosslinked silicone elastomer powder that is spherical and prepared by
(1) preparing crosslinkable siloxane by reacting
(a) α, ω-dihydroxypoly(diorganosiloxane) having a viscosity of about 5 to about 3000 mPa·s (25° C.); and
(b) organotrialkoxysilane with a general formula R¹Si(OR²)₃;
wherein:
R¹ is a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
R² is methyl, ethyl, or 2-methoxyethyl;
(2) emulsifying the crosslinkable siloxane in the presence of a surfactant;
(3) crosslinking the emulsified siloxane to form crosslinked silicone elastomer emulsion; and
(4) drying the crosslinked silicone elastomer emulsion to isolate solid crosslinked silicone elastomer powder;
wherein the personal care composition is free of a polyether compound.

20. The personal care composition of claim 19, wherein the crosslinked elastomer powder is free of surfactant.

21. A personal care composition comprising a crosslinked silicone elastomer prepared by
(1) preparing crosslinkable siloxane by reacting
(a) α, ω-dihydroxypoly(diorganosiloxane) having a viscosity of about 5 to about 3000 mPa·s (25° C.); and
(b) organotrialkoxysilane with a general formula R¹Si(OR²)₃;
wherein:
R¹ is a substituted or unsubstituted alkyl group, a substituted or unsubstituted alkenyl group, or a substituted or unsubstituted aryl group, and wherein the substituted alkyl group is halogen substituted alkyl group with 1 to 4 carbon atoms;
R² is methyl, ethyl, or 2-methoxyethyl;
wherein the alkoxyl group of component (b) is about 1.5 to about 5 per silanol groups of component (a);
(2) emulsifying the crosslinkable siloxane in the presence of a surfactant; and
(3) crosslinking the emulsified siloxane;
wherein the personal care composition is free of a polyether compound.

* * * * *